（12） United States Patent
Kurochi et al.

(10) Patent No.: US 9,020,093 B2
(45) Date of Patent: Apr. 28, 2015

(54) TWO-DIMENSIONAL COLLIMATOR MODULE, X-RAY DETECTOR, X-RAY CT APPARATUS, AND METHOD FOR ASSEMBLING TWO-DIMENSIONAL COLLIMATOR MODULE

(75) Inventors: Haruo Kurochi, Tokyo (JP); Takayuki Koike, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 494 days.

(21) Appl. No.: 13/407,069

(22) Filed: Feb. 28, 2012

(65) Prior Publication Data

US 2012/0219107 A1 Aug. 30, 2012

(30) Foreign Application Priority Data

Feb. 28, 2011 (JP) .................. 2011-041710

(51) Int. Cl.
*G21K 1/02* (2006.01)
*A61B 6/00* (2006.01)

(52) U.S. Cl.
CPC ............... *G21K 1/025* (2013.01); *A61B 6/4291* (2013.01); *G21K 1/02* (2013.01)

(58) Field of Classification Search
CPC .......... A61B 6/06; A61B 6/4291; G21K 1/00; G21K 1/02; G21K 1/025; G01T 1/16; G01T 1/161; G01T 1/1614; G01T 1/1618
USPC ........... 378/19, 145, 147, 149, 189, 204, 210; 359/641
See application file for complete search history.

(56) References Cited

U.S. PATENT DOCUMENTS

| 5,099,134 | A | * | 3/1992 | Hase et al. ............. 250/505.1 |
| 5,198,680 | A | | 3/1993 | Kurakake |
| 6,363,136 | B1 | | 3/2002 | Flisikowski et al. |
| 7,362,849 | B2 | | 4/2008 | Short et al. |
| 7,702,073 | B2 | | 4/2010 | Harding |
| 7,869,573 | B2 | | 1/2011 | Banchieri |
| 7,889,845 | B2 | | 2/2011 | Harding |
| 8,451,977 | B2 | * | 5/2013 | Kurochi .................... 378/147 |
| 2006/0233298 | A1 | | 10/2006 | Igarashi et al. |
| 2009/0168968 | A1 | | 7/2009 | Banchieri |
| 2009/0225955 | A1 | * | 9/2009 | Igarashi et al. ............ 378/149 |
| 2010/0014642 | A1 | | 1/2010 | Halazonetis et al. |

(Continued)

FOREIGN PATENT DOCUMENTS

| CN | 1672039 A | 9/2005 |
| JP | 2010127630 | 6/2010 |

*Primary Examiner* — Anastasia Midkiff
(74) *Attorney, Agent, or Firm* — Armstrong Teasdale LLP

(57) ABSTRACT

A two-dimensional collimator module is provided. The two-dimensional collimator module includes first collimator plates arranged in a channel direction, second collimator plates arranged in a slice direction and combined with the first collimator plates to form a lattice, and a first block and a second block that hold the first collimator plates, wherein each of the first collimator plates is formed with slits, each of the second collimator plates is inserted through an associated row of the slits, first plate surfaces of the second collimator plates in the slice direction abut only first wall surfaces of first and second wall surfaces of the slits in the slice direction in a first set of the first collimator plates, and second plate surfaces of the second collimator plates opposite to the first plate surfaces abut only the second wall surfaces of the slits in a second set of first collimator plates.

20 Claims, 16 Drawing Sheets

(56) References Cited

U.S. PATENT DOCUMENTS

| | | |
|---|---|---|
| 2010/0158195 A1 | 6/2010 | Wirth |
| 2010/0239072 A1 | 9/2010 | Kurochi |
| 2012/0069954 A1* | 3/2012 | Iso et al. .......................... 378/7 |
| 2012/0087462 A1* | 4/2012 | Ikhlef ............................... 378/4 |

* cited by examiner

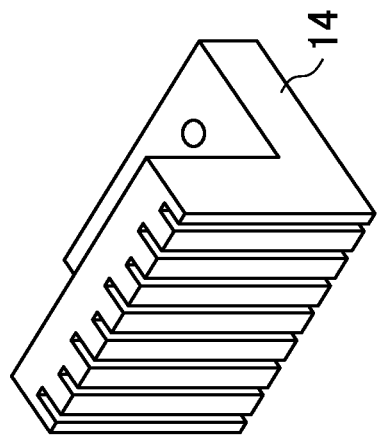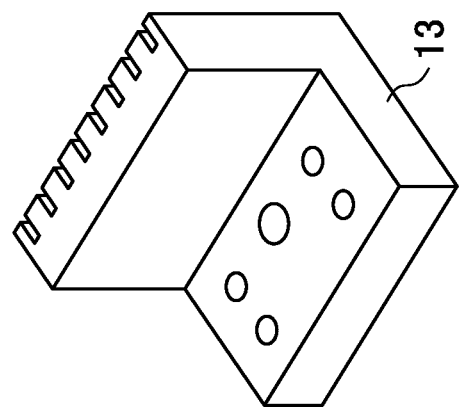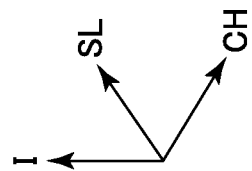
FIG. 6

TWO-DIMENSIONAL COLLIMATOR MODULE, X-RAY DETECTOR, X-RAY CT APPARATUS, AND METHOD FOR ASSEMBLING TWO-DIMENSIONAL COLLIMATOR MODULE

CROSS REFERENCE TO RELATED APPLICATIONS

This application claims the benefit of Japanese Patent Application No. 2011-041710 filed Feb. 28, 2011, which is hereby incorporated by reference in its entirety.

BACKGROUND OF THE INVENTION

The present invention relates to a two-dimensional collimator module, an X-ray detector, an X-ray CT (Computed Tomography) apparatus, a method for assembling the two-dimensional collimator module, and a method for producing a two-dimensional collimator device.

In recent years, in an X-ray CT apparatus, the number of rows of X-ray detectors has increased so that the influence of scattered radiation in a slice direction has become serious. Accordingly, as a collimator for removing scattered radiation to be disposed on the X-ray incident surface side of each of the X-ray detectors, various two-dimensional collimators have been proposed in which a plurality of collimator plates are arranged not only in a channel direction, i.e., the direction of the fan angle of an X-ray, but also in the slice direction.

For example, a two-dimensional collimator has been proposed in which channel-direction collimator plates and slice-direction collimator plates are combined into a lattice-like configuration (see, e.g., Japanese Unexamined Patent Publication No. 2010-127630, FIGS. 1 to 7).

However, each of the two-dimensional collimators proposed so far is hard to assemble or machining therefor is difficult, and it is not easy to increase the positional accuracy thereof. For example, in the example of Japanese Unexamined Patent Publication No. 2010-127630, it is difficult to form slits by machining and, unless a groove width having a sufficient margin with respect to the plate thickness of the collimator in the slice direction is provided, it is difficult to insert, for example, several hundreds of slice-direction collimator plates into several tens of channel-direction collimator plates. However, if a sufficient margin is allowed for the groove width, the collimator plates incur a positional error or an inclination error.

Under such circumstances, a two-dimensional collimator module is in demand which allows the removal of scattered radiation in the channel direction and in the slice direction, is easy to assemble, and has high positional accuracy.

BRIEF DESCRIPTION OF THE INVENTION

In a first aspect, a two-dimensional collimator module is provided. The collimator module includes a plurality of first collimator plates arranged in a channel direction, a plurality of second collimator plates arranged in a slice direction and combined with the plurality of first collimator plates so as to form a lattice, and a first block and a second block which hold the plurality of first collimator plates placed therebetween in the slice direction, wherein each of the plurality of first collimator plates is formed with a plurality of slits each extending along a direction of radiation from an X-ray focal spot and arranged in the slice direction, each of the plurality of second collimator plates is inserted through each row of the slits in the plurality of first collimator plates which are arranged in a channel direction, one-side plate surfaces of the second collimator plates in the slice direction abut only on one wall surfaces of the two wall surfaces of the slits in the slice direction in some of the plurality of first collimator plates, and the other-side plate surfaces of the second collimator plates opposite to the one-side plate surfaces thereof in the slice direction abut only on the other wall surfaces of the two wall surfaces of the slits in the slice direction in the other first collimator plates included in the plurality of first collimator plates and other than the some first collimator plates.

In a second aspect, the two-dimensional collimator module according to the first aspect described above is provided, wherein each of the respective surfaces of the first and second blocks opposing each other is formed with a plurality of grooves into which the first collimator plates are to be inserted.

In a third aspect, the two-dimensional collimator module according to the second aspect described above is provided, wherein the plurality of grooves formed in the first block include grooves having equal depths in the slice direction, the plurality of grooves formed in the second block include grooves each having a first depth in the slice direction and grooves each having a second depth larger than the first depth in the slice direction, the some first collimator plates or the other first collimator plates are inserted in the grooves each having the first depth to abut on the wall surfaces of the grooves in the slice direction, and the remaining ones of the some first collimator plates and the other first collimator plates are inserted into the grooves each having the second depth to have respective spaces between themselves and the wall surfaces of the grooves in the slice direction.

In a fourth aspect, the two-dimensional collimator module according to the third aspect described above is provided, wherein the grooves each having the first depth and the grooves each having the second depth are alternately arranged in the channel direction.

In a fifth aspect, the two-dimensional collimator module according to the second aspect described above is provided, wherein the plurality of grooves formed in the first block include grooves having equal depths in the slice direction, the plurality of grooves formed in the second block include grooves having equal depths in the slice direction, the plurality of first collimator plates include collimator plates each having a first length in the slice direction and collimator plates each having a second length shorter than the first length in the slice direction, the some first collimator plates or the other first collimator plates are the collimator plates each having the first length and abut on at least either of the both slice direction wall surfaces of the grooves in which they are inserted, and the remaining ones of the some first collimator plates and the other first collimator plates are the collimator plates each having the second length and have respective spaces between themselves and the slice direction wall surfaces of the grooves in which they are inserted.

In a sixth aspect, the two-dimensional collimator module according to any one of the first to fifth aspects described above is provided, which has a fixing sheet to be bonded to the plurality of first collimator plates on at least one of an X-ray incident surface side and an X-ray emission surface side of the two-dimensional collimator module.

In a seventh aspect, the two-dimensional collimator module according to any one of the first to sixth aspects described above is provided, wherein the plurality of first collimator plates are arranged in a fan-like configuration along the channel direction.

In an eighth aspect, the two-dimensional collimator module according to any one of the first to seventh aspects described above is provided, wherein each of the plurality of first collimator plates has a fan-like main portion along a direction of a corn angle of an X-ray beam from the X-ray focal spot.

In a ninth aspect, the two-dimensional collimator module according to any one of the first to eighth aspects described above is provided, wherein the plurality of second collimator plates are arranged in a fan-like configuration along the direction of the corn angle of the X-ray beam from the X-ray focal spot.

In a tenth aspect, the two-dimensional collimator module according to any one of the first to ninth aspects described above is provided, wherein each of the plurality of second collimator plates has a fan-like main portion along the channel direction.

In an eleventh aspect, the two-dimensional collimator module according to any one of the first to tenth aspects described above is provided, wherein each of the plurality of second collimator plates has an end portion wider than a length of each of the slits at one end thereof in the channel direction.

In a twelfth aspect, the two-dimensional collimator module according to any one of the first to eleventh aspects described above is provided, wherein a plate thickness of each of the second collimator plates is 0.06 mm to 0.22 mm, and a width of each of the slits is 0.1 mm to 0.28 mm and larger than the plate thickness.

In a thirteenth aspect, the two-dimensional collimator module according to the twelfth aspect described above is provided, wherein the width of the slit is 0.20 mm to 0.28 mm.

In a fourteenth aspect, an X-ray detector is provided. The X-ray detector includes a plurality of the two-dimensional collimator modules according to any one of the first to thirteenth aspects described above which are disposed on an X-ray incident surface side thereof.

In a fifteenth aspect, an X-ray CT apparatus is provided. The X-ray CT apparatus includes the X-ray detector according to the fourteenth aspect described above.

In a sixteenth aspect, a method for assembling a two-dimensional collimator module is provided. The method includes inserting a plurality of first collimator plates into a plurality of grooves formed in each of the respective surfaces of a first block and a second block opposing each other, moving the plurality of first collimator plates toward the first block to thereby cause the plurality of first collimator plates to abut on walls surface of the grooves in the first block and align positions of a plurality of slits formed in the first collimator plates, inserting each of a plurality of second collimator plates through each row of the slits having their positions aligned, moving the plurality of first collimator plates toward the second block to thereby cause some of the plurality of first collimator plates to abut on wall surfaces of the grooves in the second block and also bring the other first collimator plates included in the plurality of first collimator plates and other than the some first collimator plates closer to the wall surfaces of the grooves in the second block to allow the second collimator plates to be held between wall surfaces of the slits in the some first collimator plates and wall surfaces of the slits in the other first collimator plates, and bonding the first and second blocks and the plurality of first collimator plates to each other, while bonding the plurality of first collimator plates and the plurality of second collimator plates to each other.

In a seventeenth aspect, a method for producing a two-dimensional collimator device is provided. The method includes assembling a plurality of the two-dimensional collimator modules in accordance with the assembling method according to the sixteenth aspect described above, and disposing the plurality of two-dimensional collimator modules in a channel direction.

In accordance with the foregoing aspects, the second collimator plates are inserted through the slits in the first collimator plates and held between the wall surfaces thereof, thereby allowing successful positioning to be performed between the first collimator plates and the second collimator plates. Therefore, it is possible to provide a two-dimensional collimator module which allows the removal of scattered radiation in the channel direction and in the slice direction, is easy to assemble, and has high positional accuracy.

BRIEF DESCRIPTION OF THE DRAWINGS

FIG. 6 is a view illustrating determining the positions of a top-end block and a bottom-end block.

DETAILED DESCRIPTION OF THE INVENTION

A detailed description of an exemplary embodiment is provided herein.

Figure 1:
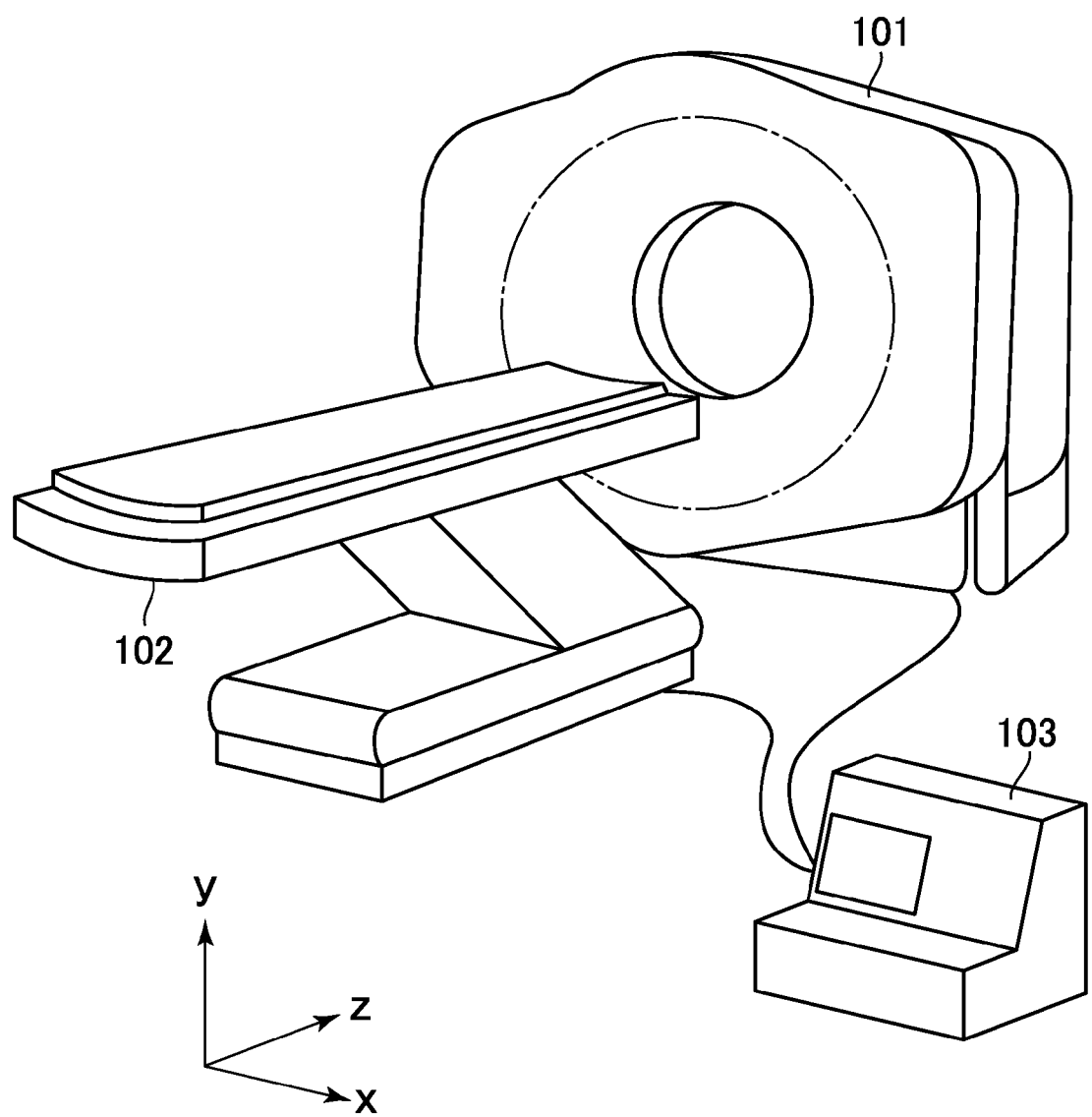
FIG. 1 is an outer appearance view of an X-ray CT apparatus.

FIG. 1 is an outer appearance view of an X-ray CT apparatus 100. As shown in FIG. 1, the X-ray CT apparatus 100 has a scan gantry 101 for scanning a subject and collecting projection data, and a cradle 102 for carrying the subject placed thereon and moving into and out of a bore in the scan gantry 101 as a tomographic space. The X-ray CT apparatus 100 further includes an operation console 103 for allowing the operation of the X-ray CT apparatus 100 and reconstructing an image based on the collected projection data.

The cradle 102 has a motor embedded therein for linearly moving the cradle 102 in a vertical direction and in a horizontal direction. The cradle 102 carries the subject placed thereon and moves into and out of the bore in the scan gantry 101.

The operation console 103 includes an input unit for receiving an input from an operator and a monitor for displaying an image. The operation console 103 also internally includes a central processing unit for performing control of each of the components for collecting the projection data of the subject, a three-dimensional image reconstructing process, and the like. The operation console 103 also internally includes a data collection buffer for collecting the data acquired in the scan gantry 101, and a storage unit for storing a program, data, and the like.

The scan gantry 101 has an X-ray tube for scanning the subject and an X-ray detection unit.

Figure 2:
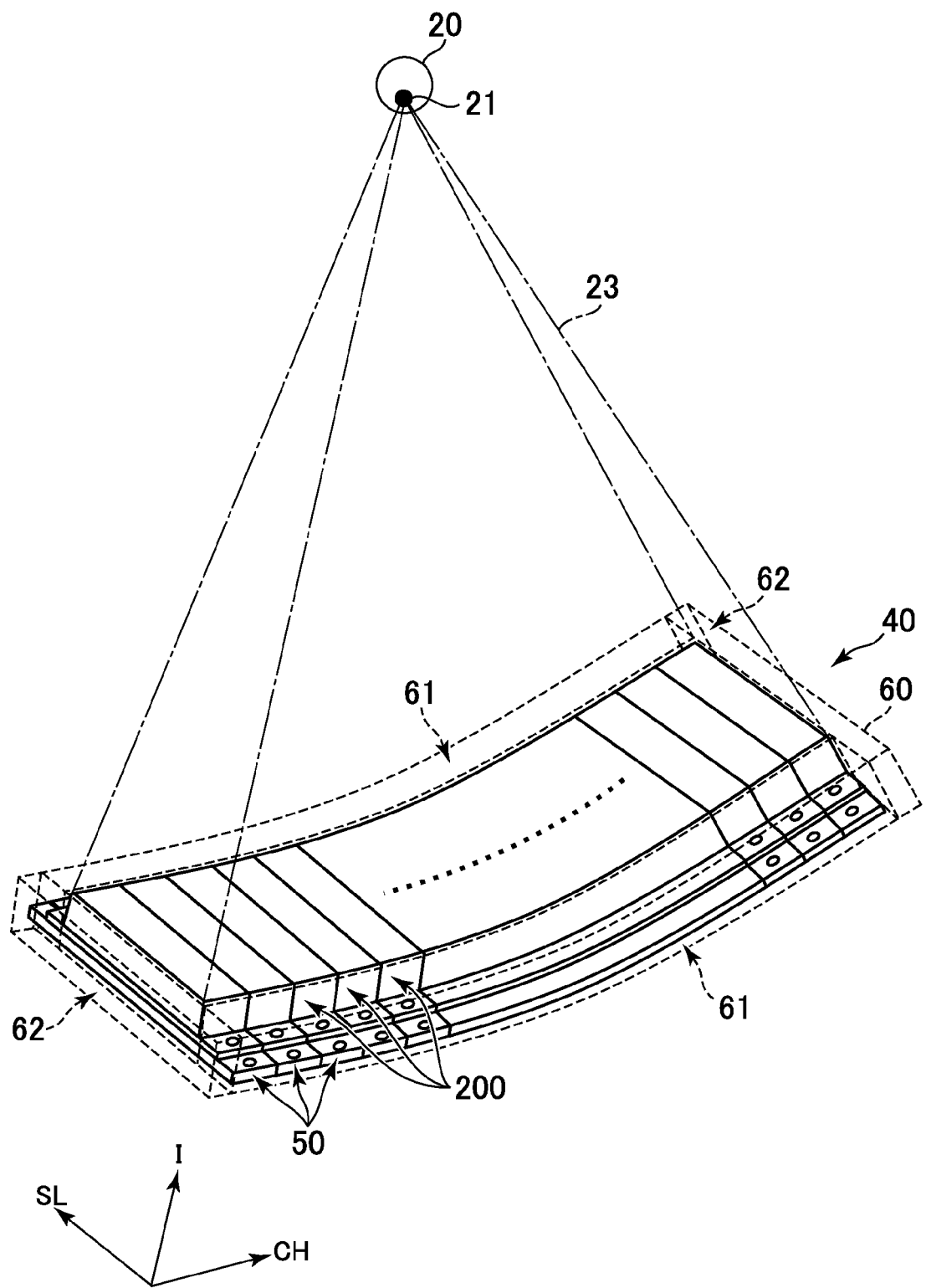
FIG. 2 is a view showing an X-ray tube and an X-ray detection unit.

FIG. 2 is a view showing the X-ray tube and the X-ray detection unit. Here, as shown in FIG. 2, it is assumed that the direction (direction of the horizontal movement of the cradle 102 or direction of the body axis of the subject) of the rotation axis of the scan gantry 101 is a slice direction SL, and the direction of the fan angle of an X-ray beam 23 is a channel direction CH. It is also assumed that the direction orthogonal to the channel direction CH and the slice direction SL and directed toward the rotation center of the scan gantry 101 is an isocenter direction I. Note that, with regard to each of the channel direction CH, the slice direction SL, and the isocenter direction, a direction indicated by an arrow is assumed to be a positive (+) direction and a direction opposite thereto is assumed to be a negative (−) direction.

An X-ray detection unit 40 has a plurality of X-ray detector modules 50 for detecting an X-ray, a plurality of two-dimensional collimator modules 200 for collimating the X-ray beam 23 from an X-ray focal spot 21 in the X-ray tube 20, and a base portion 60 for fixing the plurality of X-ray detector modules 50 and the plurality of two-dimensional collimator modules 200 to reference positions.

The plurality of two-dimensional collimator modules 200 are disposed along the channel direction CH to form a two-dimensional collimator device. The plurality of X-ray detector modules 50 are arranged along the channel direction CH relative to the plurality of two-dimensional collimator modules 200. Each of the X-ray detector modules 50 is mounted with respect to each of the two-dimensional collimator modules 200 in one-to-one correspondence and provided on the X-ray emission side of the two-dimensional collimator module 200. The X-ray detector modules 50 detect the X-ray beam transmitted through the subject that has been placed on the cradle 102 and transported into the bore.

Each of the X-ray detector modules 50 has a scintillator block (not shown) for receiving the X-ray and emitting visible light and a photo diode chip (not shown) in which photo diodes for performing photoelectric conversion are two-dimensionally arranged along the channel direction CH and along the slice direction SL. Also, each of the X-ray detector modules 50 has a semiconductor chip (not shown) which has the function of accumulating outputs from the photodiode chip provided on a substrate and performing output switching for changing a slice thickness.

The base portion 60 has a rectangular frame-like shape, and includes a pair of arcuate base materials 61 and a pair of linear base materials 62 connecting the end portions of the base materials 61. The base materials 61 are also provided with base-side positioning pins or positioning holes for determining the positions of the plurality of two-dimensional collimator modules 200.

In the base portion 60, a length in the slice direction SL may be, for example, 350 mm to 400 mm, a thickness may be, for example 35 mm to 40 mm, and the length of an internal space formed by the base materials 61 and the base materials 62 may be, for example 300 mm to 350 mm. The width of each of the two-dimensional collimator modules 200 in the channel direction CH may be, for example 50 mm. The details of the two-dimensional collimator module 200 will be described later.

Examples of a material for the base portion 60 that can be used include an aluminum alloy, a carbon fiber-reinforced plastic (CFRP) which is a composite material of carbon fiber and a thermoplastic resin, and the like. Each of the aluminum alloy and the CFRP is light-weight and strong and has high durability so that, when the base portion 60 rotates at a high speed in the scan gantry 101 of the X-ray CT apparatus 100, it can rotate without producing an unnecessary eccentric force. In addition, the base portion 60 is less likely to be distorted and the two-dimensional collimator modules 200 fixed thereto are also less likely to be distorted.

In FIG. 2, only eight of the two-dimensional collimator modules 200 are schematically depicted but, in the exemplary embodiment, several tens of the two-dimensional collimator modules 200 are fixed to the one base portion 60.

Hereinbelow, a detailed description will be given of a structure of the two-dimensional collimator module.

Figure 3:
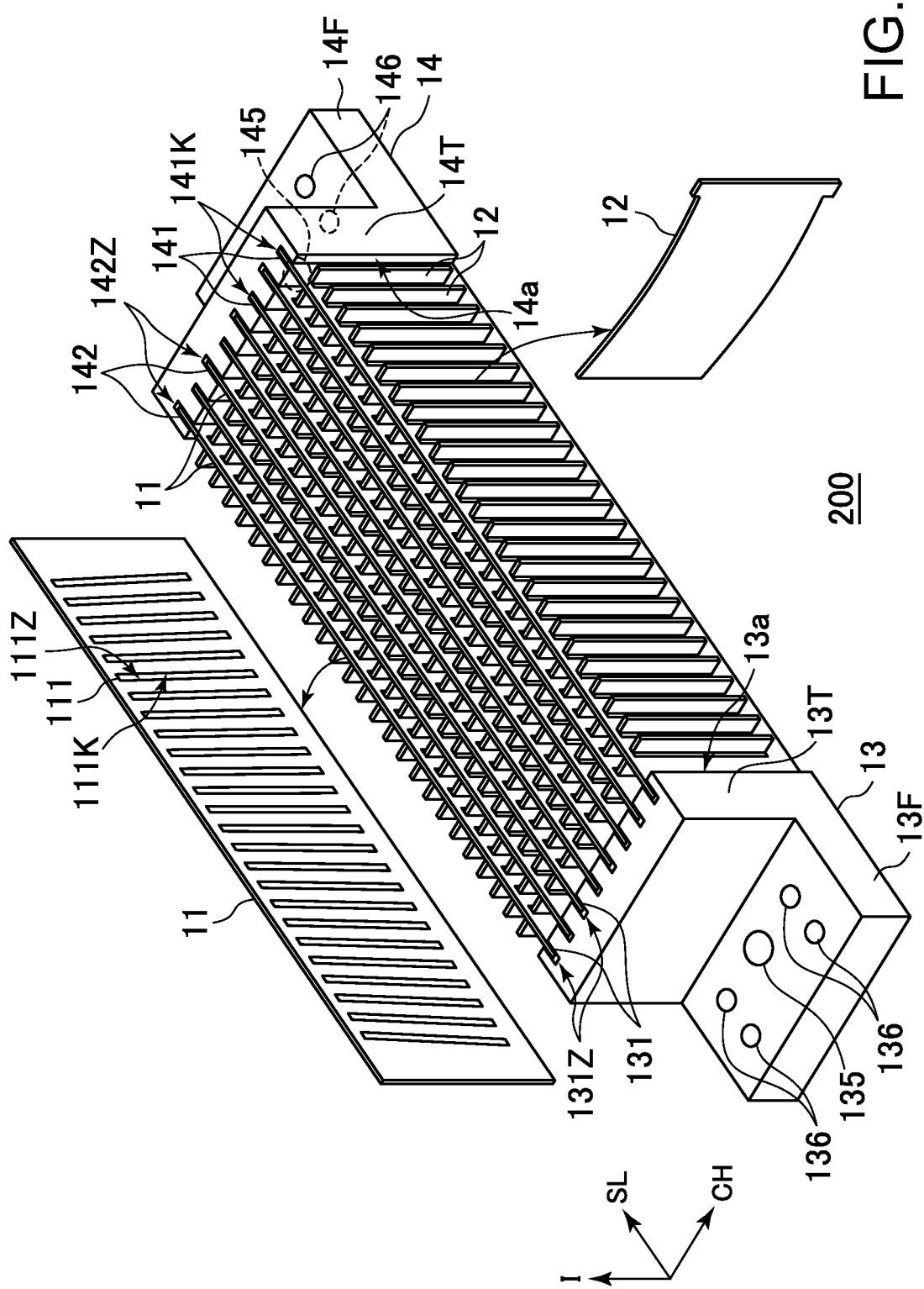
FIG. 3 is a perspective view of a two-dimensional collimator module.
Figure 4:
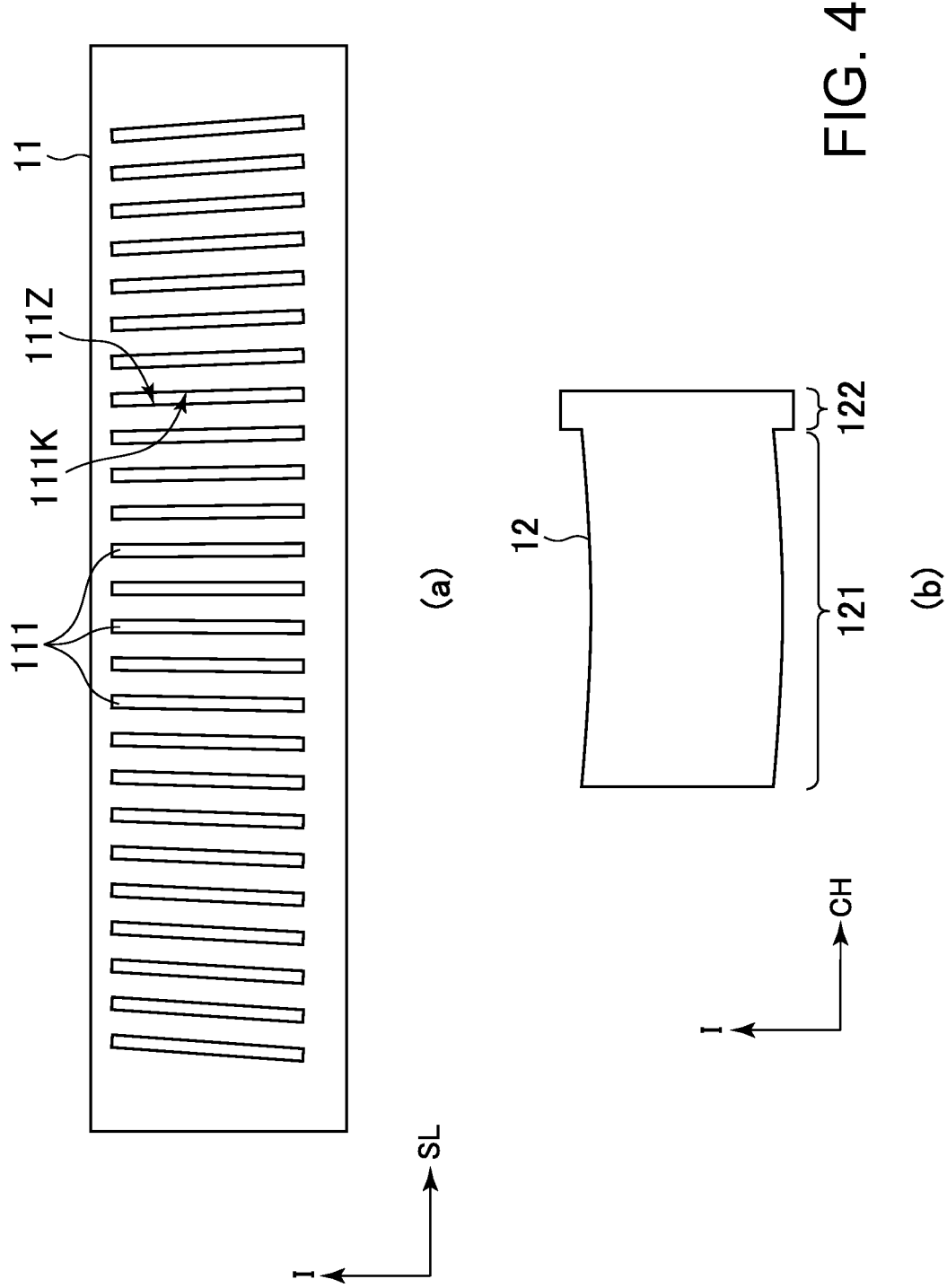
FIG. 4 is a view showing a first collimator plate and a second collimator plate.

FIG. 3 is a perspective view of the two-dimensional collimator module according to the present embodiment. FIG. 4 is a view showing a first collimator plate and a second collimator plate which form the two-dimensional collimator module.

As shown in FIG. 3, the two-dimensional collimator module 200 has a plurality of first collimator plates 11, a plurality of second collimator plates 12, a top-end block (first block) 13, and a bottom-end block (second block) 14. Note that, in FIG. 3, for clear illustration of the structure, the smaller number of first collimator plates 11 and the smaller number of second collimator plates 12 are depicted. Actually, however, the assumed number of the first collimator plates 11 is about 32 to 64 and the assumed number of the second collimator plates 12 is about 129 to 257.

The plurality of first collimator plates 11 are disposed in spaced-apart relation in the channel direction CH such that the plate surfaces thereof are generally parallel with each other.

The top end block 13 and the bottom end block 14 are disposed so as to hold the plurality of first collimator plates 11 placed therebetween in the slice direction SL.

The plurality of second collimator plates 12 are combined with the plurality of first collimator plates 11 to be generally orthogonal thereto. That is, the plurality of first collimator plates 11 and the plurality of second collimator plates 12 are combined with each other to form a lattice-like two-dimensional collimator portion.

The top-end block 13, the bottom end block 14, the plurality of first collimator plates 11, and the plurality of second collimator plates 12 have their positions each determined by a predetermined method and bonded to each other with an adhesive or the like.

A more detailed description will be given of the components of the two-dimensional collimator module.

As shown in FIG. 4, the first collimator plate 11 has a rectangular shape or a gently curved fan-like shape. The first collimator plate 11 is formed of a heavy metal which readily absorbs an X-ray such as, e.g., molybdenum, tungsten, or lead. When the two-dimensional collimator modules 200 are mounted on the base portion 60, the plate surfaces of the first collimator plates 11 become parallel with the direction of radiation of the X-ray beam 23 from the X-ray focal spot 21, and the long-side directions thereof coincide with the slice direction SL or the direction of the cone angle of the X-ray beam. Note that, here, the plate thickness of the first collimator plate 11 is about 0.2 mm.

The plate surfaces of the first collimator plate 11 are formed with a plurality of elongated holes through which the second collimator plates 12 are inserted, i.e., so-called slits 111. The plurality of slits 111 are formed to extend along the direction of radiation of the X-ray beam 23 from the X-ray focal spot 21 when the two-dimensional collimator modules 200 are mounted on the base portion 60.

To allow easy insertion of the second collimator plates 12, the width of each of the slits 111 in the slice direction SL has a sufficient margin with respect to the plate thickness of the second collimator plate 12 in the exemplary embodiment. However, if the width of the slit 111 is excessively large, the rigidity of the first collimator plate 11 decreases so that a strain tends to develop during assembly or scanning. In view of the foregoing, in the exemplary embodiment, the plate thickness of each of the second collimator plates 12 is 0.06 mm to 0.22 mm and the width of each of the slits 111 in the slice direction SL is 0.1 mm to 0.28 mm and larger than the plate thickness of each of the second collimator plates 12.

When the slits 111 are formed by wire-discharge machining, a wire to be used is selected from a 0.1 mm-diameter wire, a 0.2 mm-diameter wire, a 0.3 mm-diameter wire, and the like. However, in terms of the balance between cost and machining precision, the 0.2 mm-diameter wire is used in the exemplary embodiment. In view of this, the width of the slit 111 in the slice direction SL is about 0.2 mm to 0.28 mm.

Here, the width of the slit 111 in the slice direction SL is about 0.24 mm and the length of each of the slits 111 is about 15.4 mm.

As shown in FIG. 4, the second collimator plate 12 has a fan-like main portion 121 and a rectangular end portion 122. The second collimator plate 12 is formed of a heavy metal which readily absorbs an X-ray, similarly to the first collimator plate 11. When the two-dimensional collimator modules 200 are mounted on the base portion 60, the plate surfaces of the second collimator plates 12 become parallel with the direction of radiation of the X-ray beam 23 from the X-ray focal spot 21 and the directions of the curved long sides forming the fan-like main portion 121 thereof coincide with the channel direction CH.

As shown in FIG. 3, each of the second collimator plates 12 is inserted to extend through each row of the slits 111 in the plurality of the first collimator plates 11 which are arranged in the channel direction CH. The rectangular end portion of the second collimator plate 12 is larger than the length of the slit 111. Therefore, the rectangular end portion of the second collimator plate 12 functions as a stopper when the second collimator plate 12 is inserted through the slits 111. When the plurality of two-dimensional collimator modules 200 are mounted on the base portion 60, the leading end portions of the second collimator plates 12 in one of the adjacent two-dimensional collimator modules 200 and the rectangular end portions of the second collimator plates 12 in the other two-dimensional collimator module 200 overlap each other in the slice direction SL to form a part of the lattice-like two-dimensional collimator.

The second collimator plates 12 incur displacement due to thermal deformation or the like. When such displacement occurs, the state of being shielded from the X-ray changes to cause cross-talk between detection cells and vary the detection characteristics of the X-ray detection unit 40. To suppress these, it is effective to reduce the plate thickness of the second collimator plate 12. However, if the plate thickness is excessively reduced, the rigidity decreases and a strain tends to develop during assembly or scanning. In view of the foregoing, the plate thickness of the second collimator plate 12 may be about 0.06 mm to 0.14 mm, and more specifically, about 0.08 mm to 0.12 mm. Here, the plate thickness of the second collimator plate 12 is about 0.1 mm, while the width in the short-side direction of the second collimator plate 12 is about 15 mm.

The top-end block 13 and the bottom-end block 14 are each formed of a light-weight metal such as aluminum or a plastic.

As shown in FIG. 3, the top-end block 13 has a pillar portion 13T extending in the direction orthogonal to the channel direction CH and the slice direction SL, i.e., in the isocenter direction I and a flange portion 13F protruding in the negative (−) slice direction SL, which are integrally formed. Accordingly, the top-end block 13 has a generally inverted "letter L" shape when viewed in the −CH direction.

Likewise, the bottom-end block 14 has a pillar portion 14T extending in the isocenter direction I and a flange portion 14F protruding in the +SL direction, which are integrally formed. Accordingly, the bottom-end block 14 has a generally "letter L" shape when viewed in the negative (−) channel direction CH.

Additionally, as shown in FIG. 3, in the middles of the flange portions 13F and 14F of the top-end block 13 and the bottom-end block 14, holes for positioning are formed. In the holes, positioning pins 135 and 145 are inserted and placed. When the positioning pins 135 and 145 are fixed to intended positions, the two-dimensional collimator modules 200 are located at the reference positions in the base portion 60.

Around the positioning pin 135 (145), four positioning holes 136 (146) are formed. The four positioning holes 136 (146) are formed to allow the X-ray detection modules 50 shown in FIG. 2 to be precisely mounted.

As shown in FIG. 3, each of the surfaces 13a and 14a of the top-end block 13 and the bottom-end block 14 opposing each other is formed with a plurality of grooves into which the first collimator plates 11 are to be inserted. The plurality of grooves are formed so as to extend along the direction of radiation of the X-ray beam 23 from the X-ray focal spot 21 when the two-dimensional collimator modules 200 are mounted on the base portion 60.

The surface 13a of the top-end block 13 is formed with a plurality of first grooves 131 having equal depths in the slice direction SL. Here, the depth of each of the first grooves 131 in the slice direction SL is about 1 mm and the width thereof in the channel direction CH is about 0.24 mm.

On the other hand, the surface 14a of the bottom-end block 14 is formed with two types of grooves having different depths in the slice direction SL. Here, second grooves 141 each having a relatively shallow depth in the slice direction SL and third grooves 142 each having a relatively deep depth in the slice direction SL are formed to be alternately arranged in the channel direction CH. In the present embodiment, the second grooves 141 are formed at odd-numbered positions in the −CH direction and the third grooves 142 are formed at even-numbered positions in the −CH direction. Here, the depth of each of the second grooves 141 in the slice direction SL is about 1 mm and the width thereof in the channel direction CH is about 0.24 mm. Also, the depth of each of the third grooves 142 in the slice direction SL is about 1.5 mm and the width thereof in the channel direction CH is about 0.24 mm.

Wall surfaces 141K of the second grooves 141 in the positive (+) slice direction SL are reference surfaces and formed to have predetermined precise positional relationships with the positioning pins 135 and 145. On the other hand, wall surfaces 111K of the slits 111 in the +SL direction are reference surfaces and formed to have predetermined precise positional relationships with the end sides of the first collimator plates 11 in the slice direction SL.

The +SL direction end sides of the odd-numbered first collimator plates 11 abut on the +SL direction wall surfaces 141K of the second grooves 141. That is, the +SL direction wall surfaces 111K of the slits 111 in the odd-numbered first collimator plates 11 have their positions determined. The −SL direction end sides of the odd-numbered first collimator plates 11 do not abut on −SL direction wall surfaces 131Z of the first grooves 131, but have respective spaces between themselves and the wall surfaces 131Z.

The both end sides of the even-numbered first collimator plates 11 in the slice direction SL do not abut on the −SL direction wall surfaces 131Z of the first grooves 131 or +SL direction wall surfaces 142Z of the third grooves 142, but have respective spaces between themselves and these wall surfaces.

The +SL direction plate surfaces of the second collimator plates 12 abut only on the foregoing wall surfaces having their positions determined, i.e., the +SL direction wall surfaces 111K of the both wall surfaces of the slits 111 in the odd-numbered first collimator plates 11 in the slice direction SL.

The −SL direction plate surfaces of the second collimator plates 12 abut only on the −SL direction wall surfaces 111Z of the both wall surfaces of the slits 111 in the even-numbered first collimator plates 11 in the slice direction SL.

That is, each of the second collimator plates 12 is held between the +SL direction wall surfaces 111K of the slits 111 in the odd-numbered first collimator plates 11 and the −SL direction wall surfaces 111Z of the slits 111 in the even-numbered first collimator plates 11. In this state, the plurality of first collimator plates 11, the plurality of second collimator plates 12, the top-end block 13, and the bottom-end block 14 are bonded to each other with an adhesive.

Figure 5:
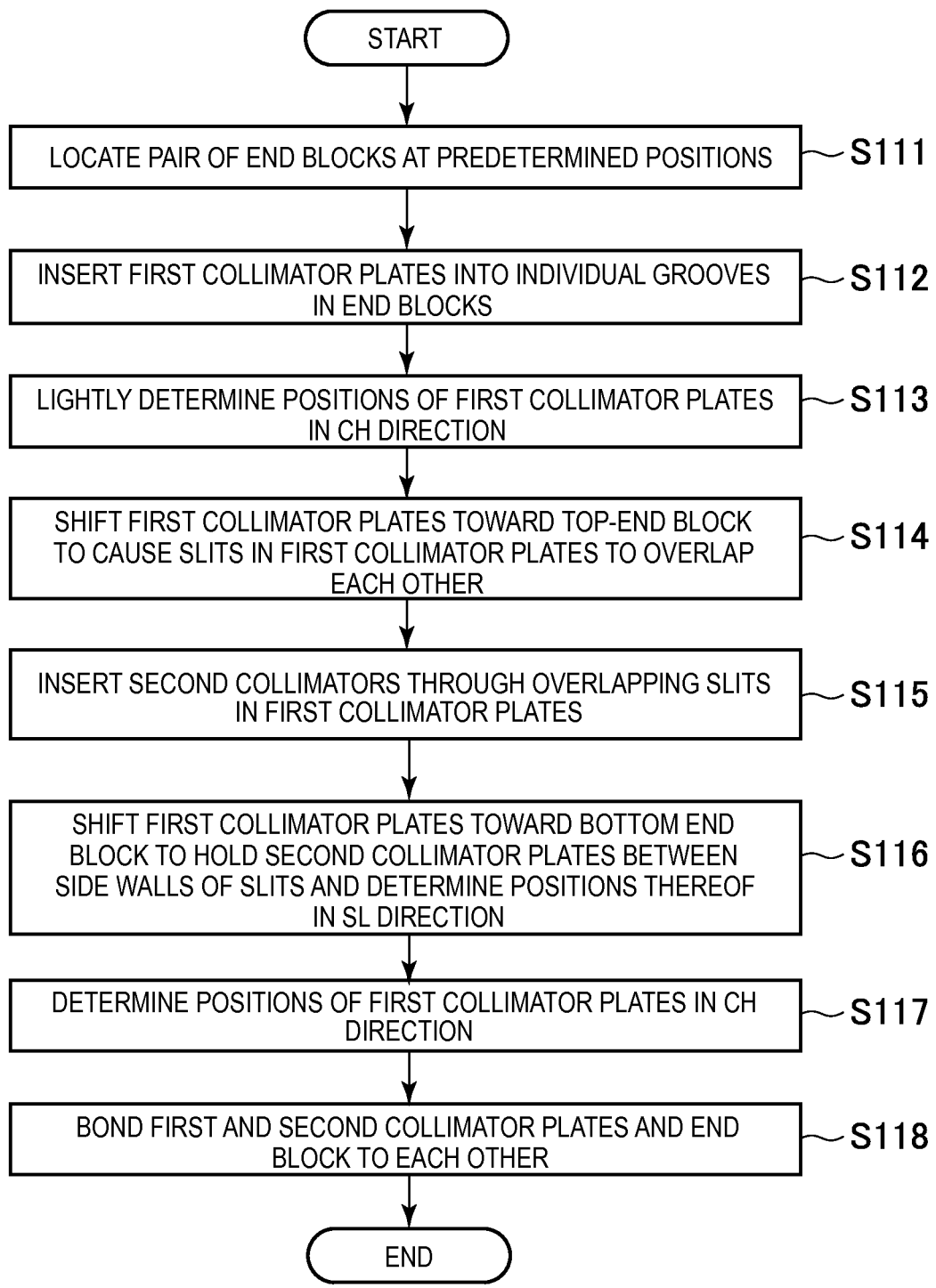
FIG. 5 is a flow chart showing a method for assembling the two-dimensional collimator module.

Hereinbelow, a description will be given of a method for assembling the two-dimensional collimator module according to the present embodiment. FIG. 5 is a flow chart showing the method for assembling the two-dimensional collimator module according to the present embodiment.

In Step S111, as shown in FIG. 6, the top-end block 13 and the bottom-end block 14 are located at the predetermined positions using a jig or the like.

Figure 7:
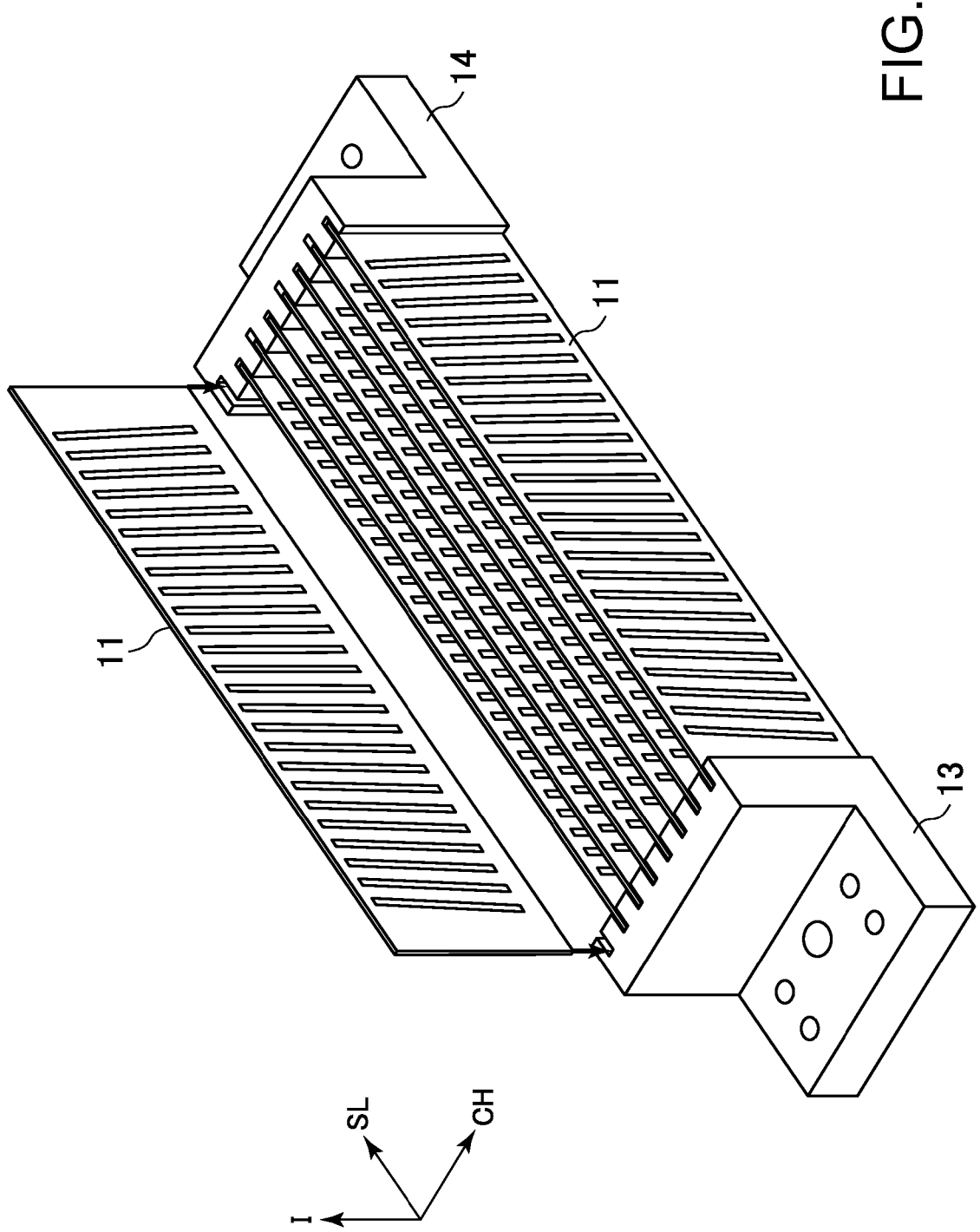
FIG. 7 is a view illustrating inserting the plurality of first collimator plates into grooves in the top-end block and the bottom-end block.

In Step S112, as shown in FIG. 7, the plurality of first collimator plates 11 are inserted into the grooves in the top-end block 13 and the bottom-end block 14.

Figure 12:
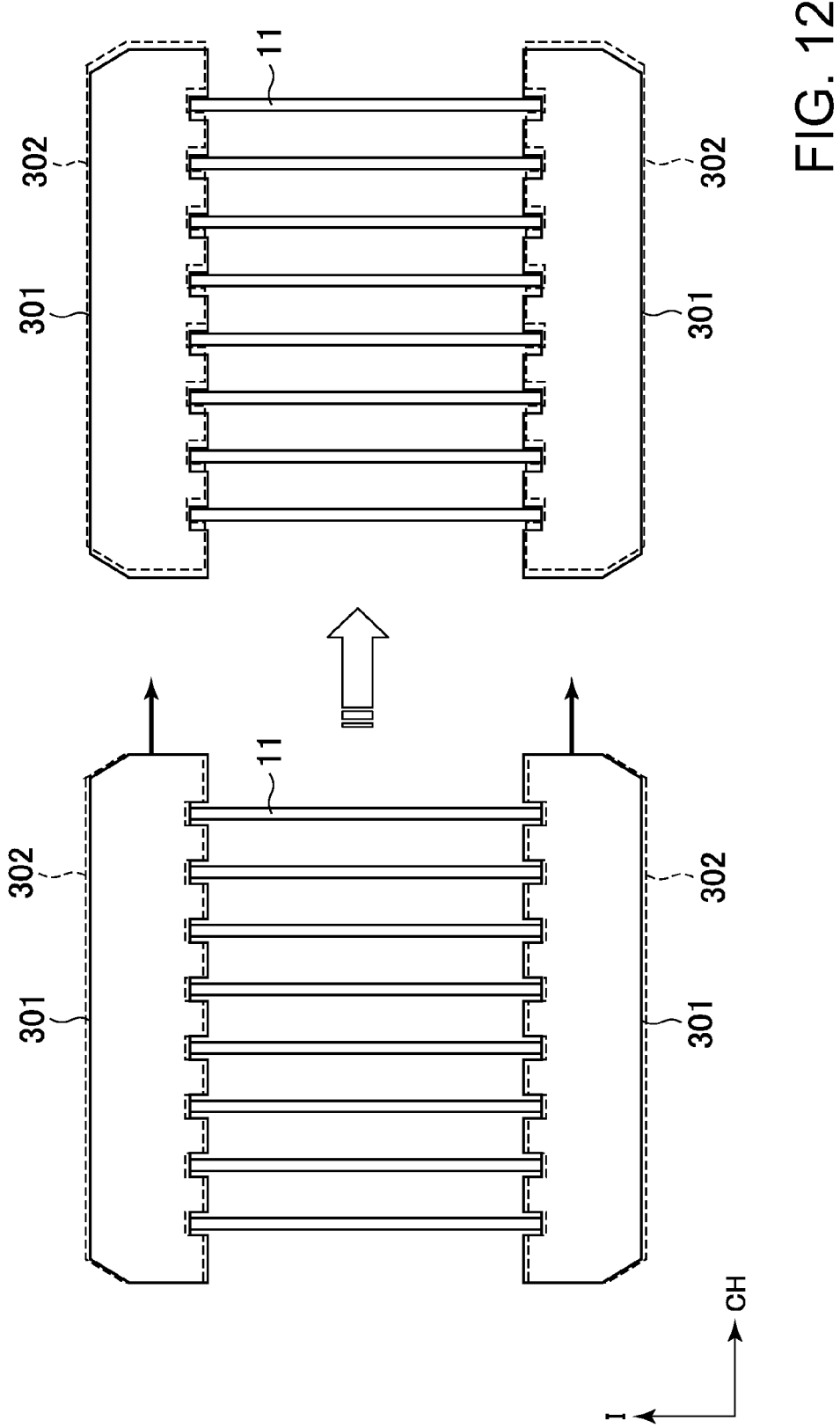
FIG. 12 is a view illustrating determining the positions of the first collimator plates.

In Step S113, the positions of the plurality of first collimator plates 11 are roughly determined using the jig or the like. For example, as shown in FIG. 12, the upper and lower ends of the first collimator plates 11 are lightly held between comb-like members 301 and 302 each having a plurality of notched portions in the channel direction CH. At this time, the first collimator plates 11 are movable in the slice direction SL.

Figure 8:
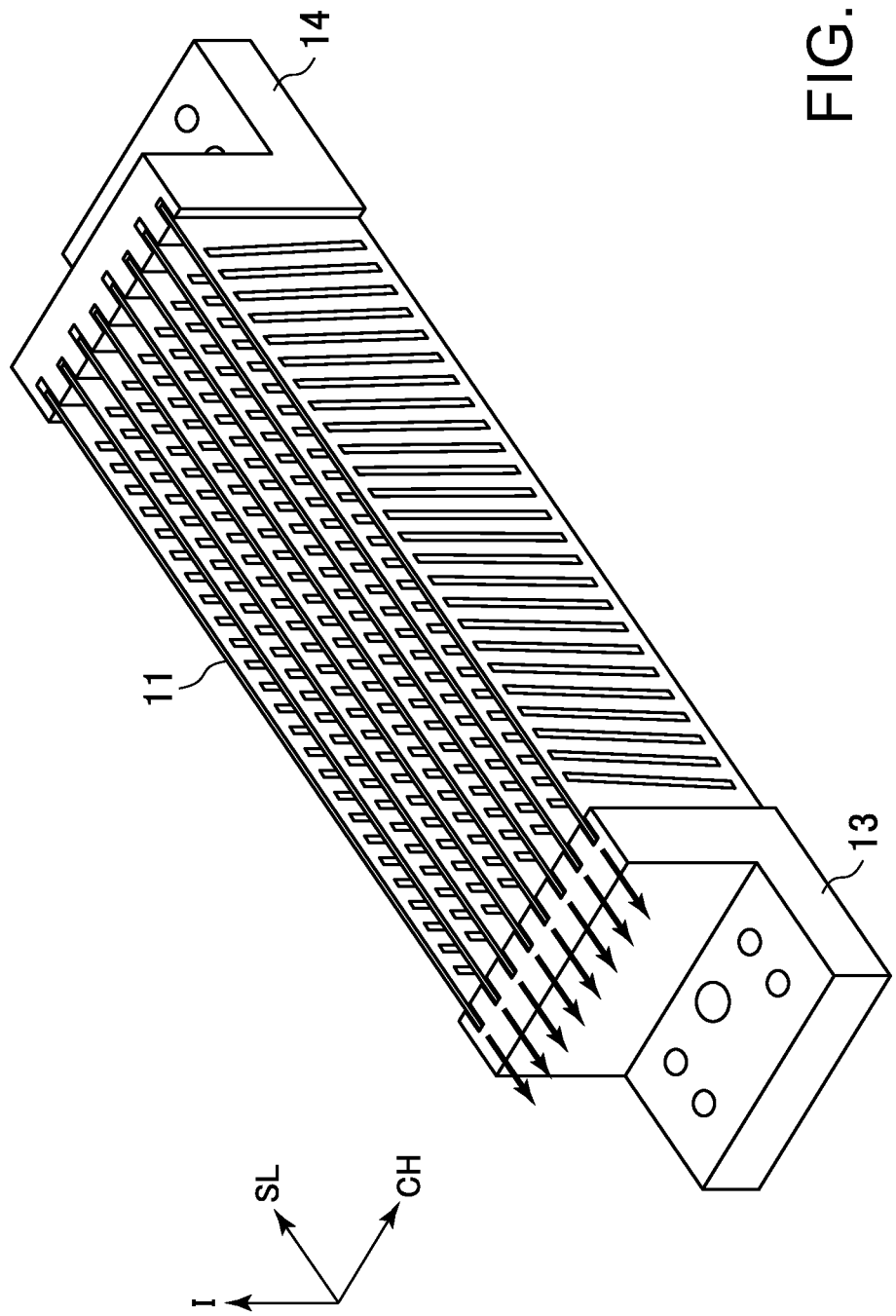
FIG. 8 is a view illustrating moving the plurality of first collimator plates toward the top-end block to align slits.
Figure 13:
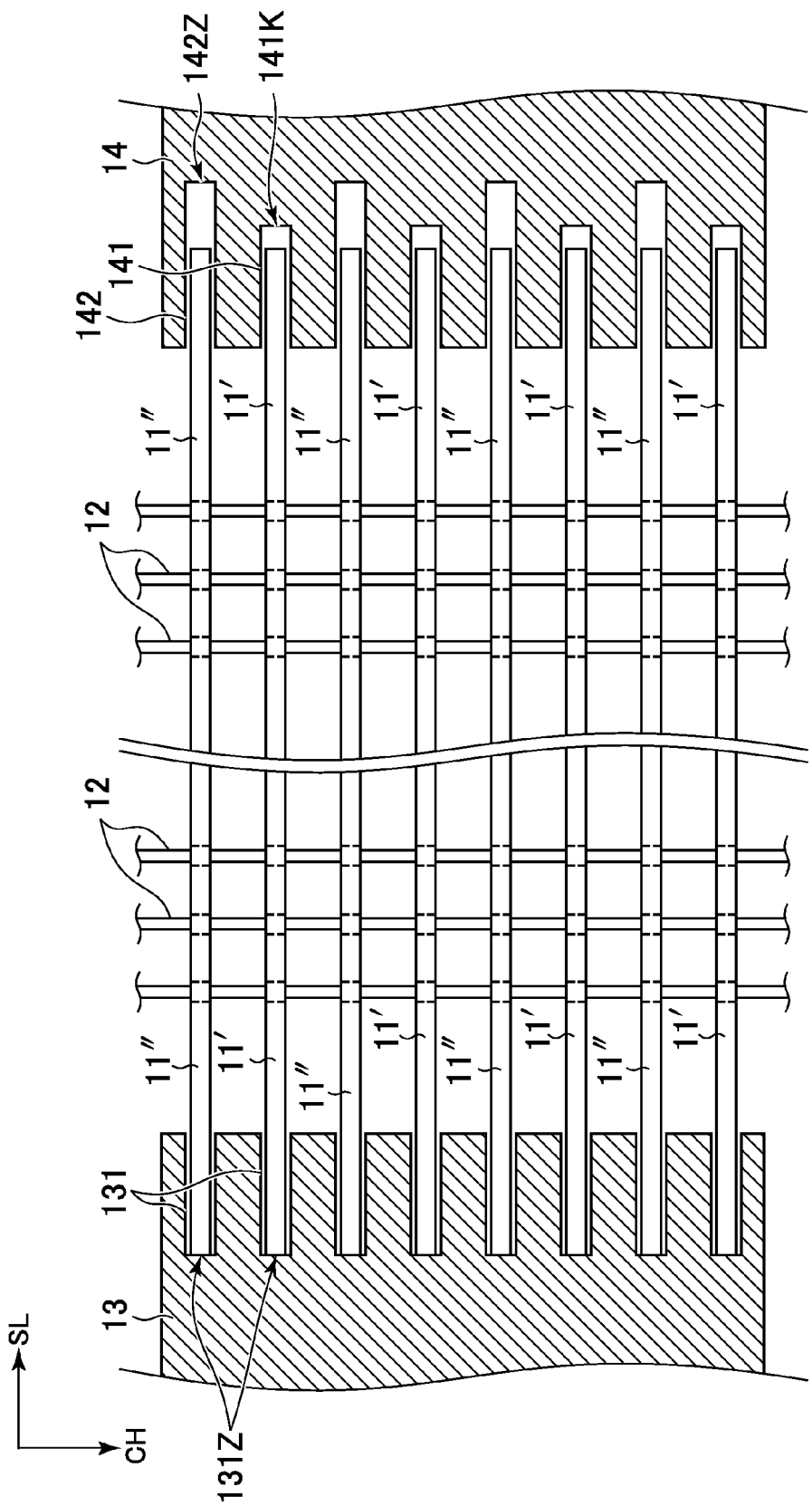
FIG. 13 is an enlarged view of the periphery of the grooves when the plurality of first collimator plates have been moved toward the top-end block.
Figure 15:
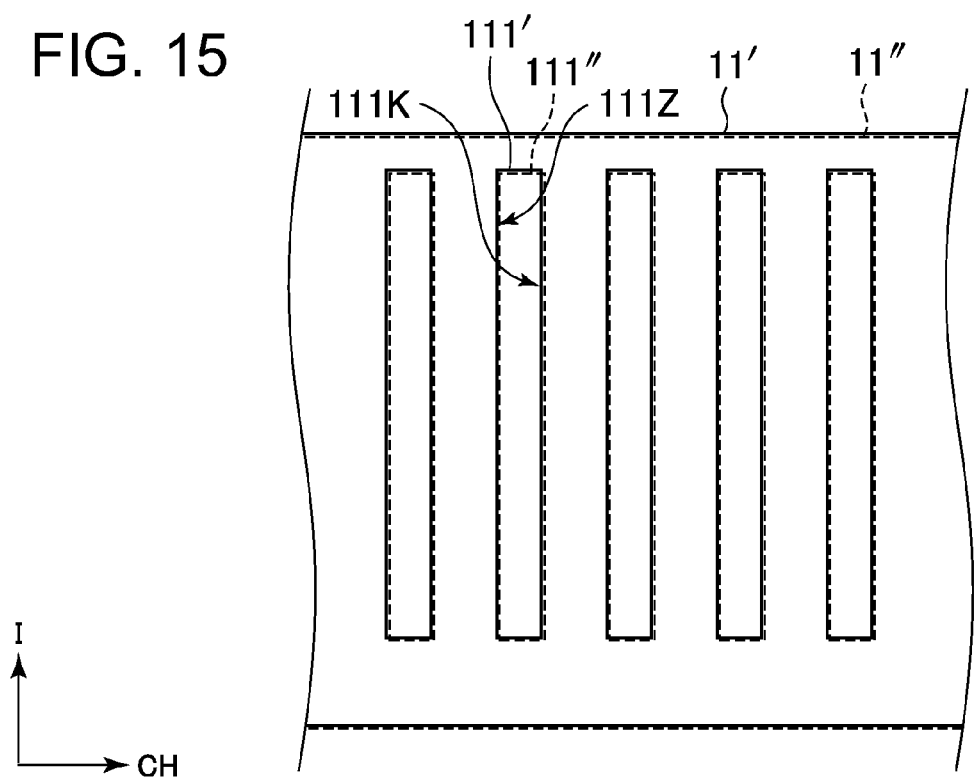
FIG. 15 is a view illustrating the positional relationship between the individual slits when the plurality of first collimator plates have been moved toward the top-end block.

In Step S114, as shown in FIG. 8, the plurality of first collimator plates 11 are moved toward the top-end block 13 (in the −SL direction). Consequently, as shown in FIG. 13, the −SL direction end sides of the first collimator plates 11 come to abut on the −SL direction wall surfaces 131Z of the first grooves 131. As a result, as shown in FIG. 15, individual slits 111' in the odd-numbered first collimator plates 11' and individual slits 111" in the even-numbered first collimator plates 11" substantially overlap each other in the channel direction CH. This allows easy insertion of the second collimator plates 12 through the slits 111.

Figure 9:
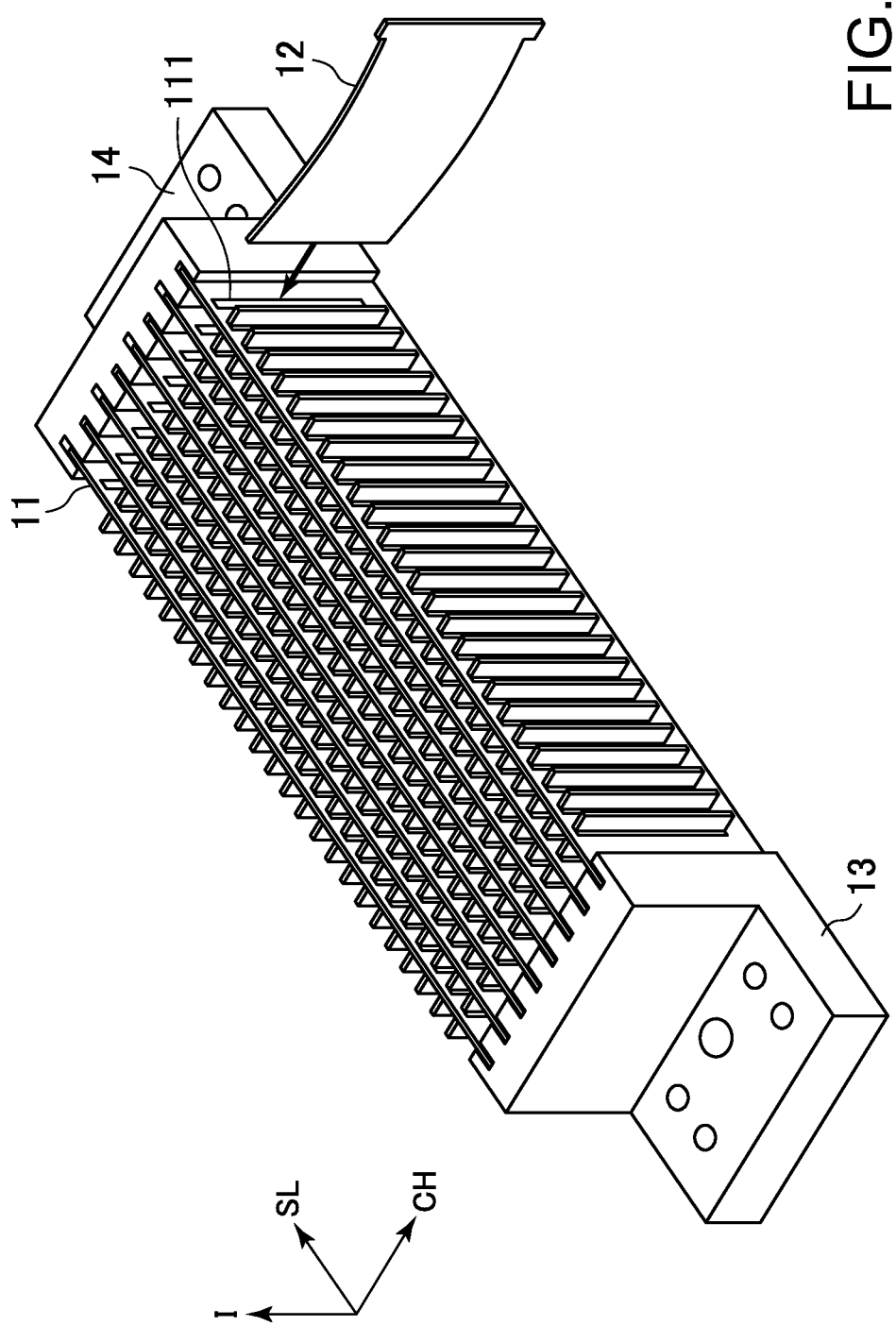
FIG. 9 is a view illustrating inserting the second collimator plates through the slits.
Figure 16:
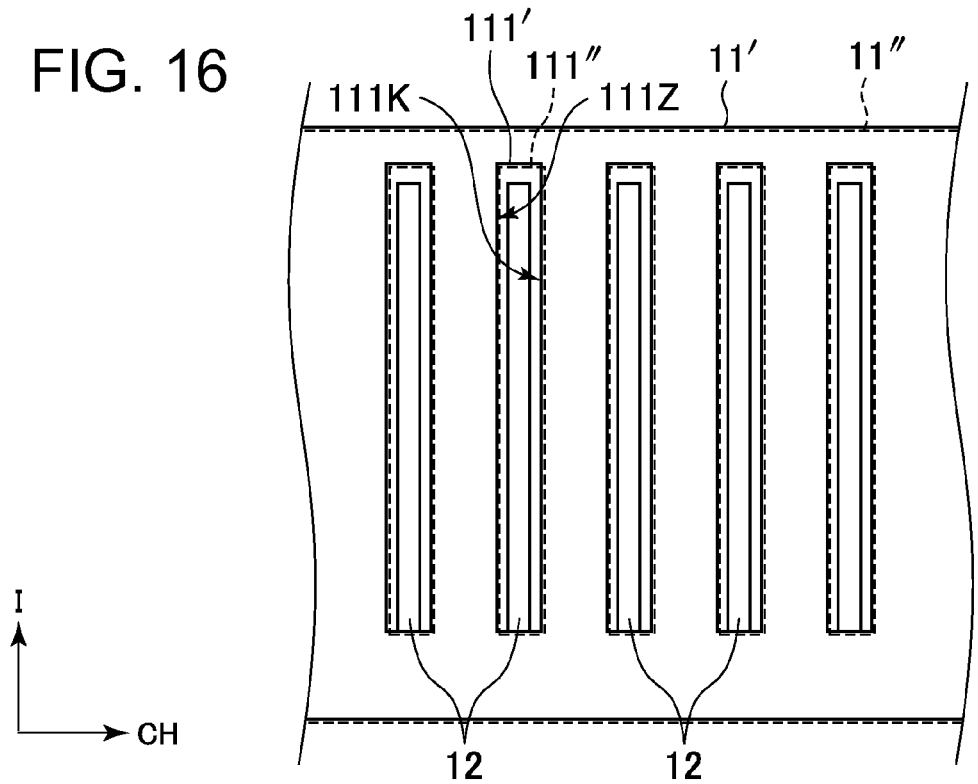
FIG. 16 is a view illustrating the positional relationship between the slits and the second collimator plates when the second collimator plates have been inserted through the slits.

In Step S115, as shown in FIG. 9, the plurality of second collimator plates 12 are inserted through the slits 111 and pushed until the second collimator plates 12 stop. In FIG. 16 is shown the positional relationships between the slits 111' in the odd-numbered first collimators 11' and the slits 111" in the even-numbered first collimator plates 11" and the second collimator plates 12 at this time.

Figure 10:
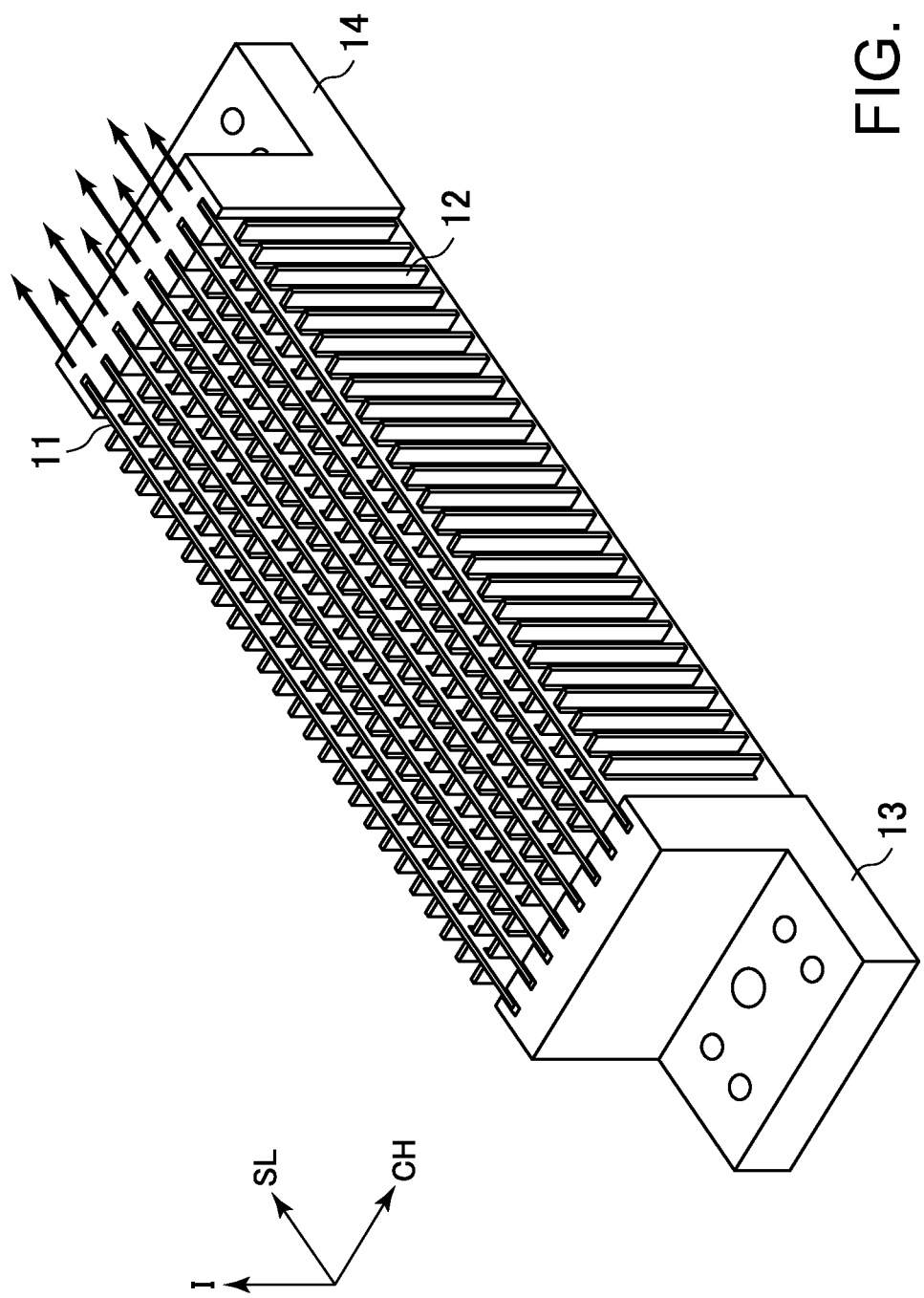
FIG. 10 is a view illustrating moving the plurality of first collimator plates 11 toward the bottom-end block.
Figure 14:
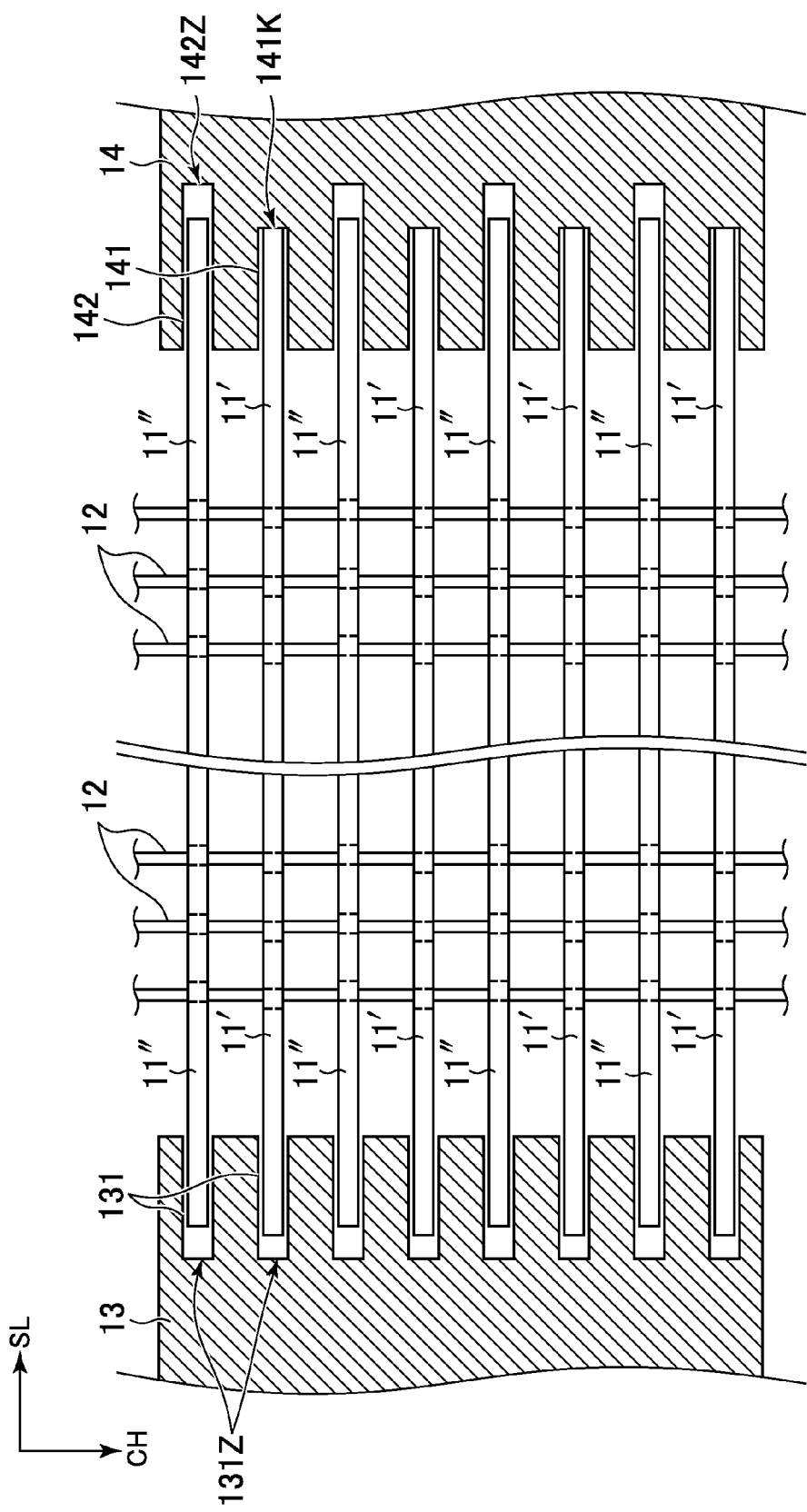
FIG. 14 is an enlarged view of the periphery of the grooves when the plurality of first collimator plates have been moved toward the bottom-end block.
Figure 17:
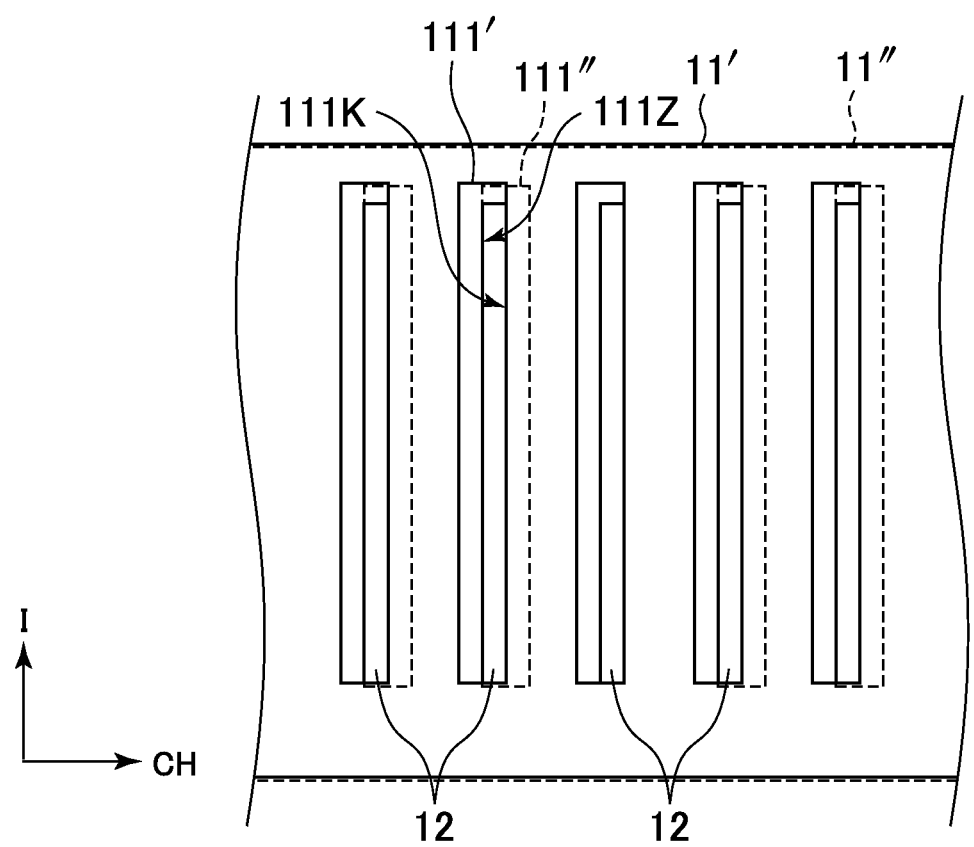
FIG. 17 is a view illustrating the positional relationship between the slits and the second collimator plates when the plurality of first collimator plates have been moved toward the bottom-end block.

In Step S116, as shown in FIG. 10, the plurality of first collimator plates 11 are moved toward the bottom end block 14 (in the +SL directions). Consequently, as shown in FIG. 14, the +SL direction end sides of the odd-numbered first collimator plates 11' come to abut on the +SL direction wall surfaces 141K of the second grooves 141. As a result, the positions of the +SL direction wall surfaces 111K of the slits 111' in the odd-numbered first collimator plates 11' are determined. On the other hand, the +SL direction end sides of the even-numbered first collimator plates 11" come closer to the +SL direction wall surfaces 142Z of the third grooves 142. The third grooves 142 are deeper than the second grooves 141, and the depth difference therebetween is larger than the difference between the width of each of the slits 111 and the plate thickness of each of the second collimator plates 12. Accordingly, the even-numbered first collimator plates 11" do not abut on the third grooves 142 and, as shown in FIG. 17, the −SL direction end sides of the slits 111" in the even-numbered first collimator plates 11" press the second collimator plates 12 inserted therein in the +SL direction. As a result, the plate surfaces of the second collimator plates 12 come to abut on the +SL direction wall surfaces 111K of the slits 111' in the odd-numbered first collimator plates 11' to determine the positions of the second collimator plates 12.

In Step S117, the positions of the plurality of first collimator plates 11 are determined again using a jig or the like. Here, using a jig as shown in FIG. 8, the upper and lower ends of the first collimator plates 11 are strongly held between the comb-like members 301 and 302 in the channel direction CH. At this time, the first collimator plates 11 are fixed.

In Step S118, in this state, the plurality of first collimator plates 11, the plurality of second collimator plates 12, the top-end block 13, and the bottom-end block 14 are bonded to each other with an adhesive or the like, whereby the two-dimensional collimator module 200 is completed.

Figure 11:
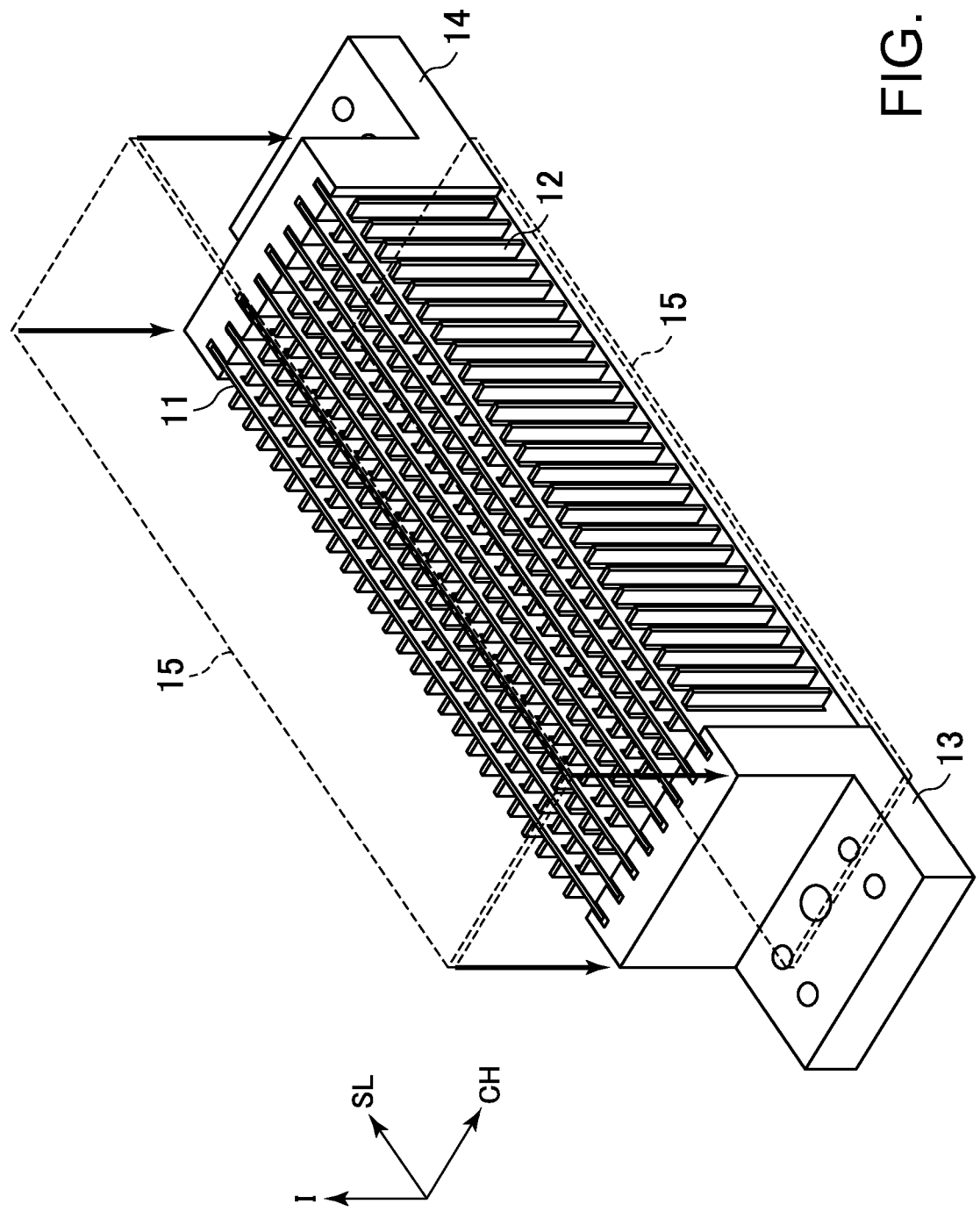
FIG. 11 is a view illustrating sticking an X-ray transmissive fixing sheet to an X-ray incident surface side and/or an X-ray emission surface side.

Note that, to further increase the rigidity of the two-dimensional collimator module 200, as shown in FIG. 11, it may also be possible to stick an X-ray transmissive fixing sheet 15 to be bonded to the plurality of first collimator plates 11 to at least one of the X-ray incident surface side and the X-ray emission surface side. The fixing sheet 15 is formed of, e.g., a carbon fiber-reinforced plastic (CFRP) having high rigidity, light weight, and high X-ray transmissivity. It may also be possible that the fixing sheet 15 is formed with, e.g., grooves corresponding to the long sides of the first collimator plates 11, and the long-side ends of the first collimator plates 11 are inserted into the grooves and bonded thereto.

Thus, according to the method for assembling the two-dimensional collimator module described above, the first collimator plates 11 are moved in the slice direction SL to align the positions of the slits 111 and allow easy insertion of the second collimator plates 12 through the slits 111, and the first collimator plates 11 and the second collimator plates 12 are pressed against the reference surfaces to allow their positions to be determined. This results in easy assembly and high positioning accuracy.

To allow easy insertion of the second collimator plates 12 through the slits 111, it is needed to sufficiently increase the width of each of the slits 111 with respect to the plate thickness of each of the second collimator plates 11. In this case, so-called allowance increases to normally degrade the accuracy of the positioning of the second collimator plates 12. Conversely, if the width of the slit 111 is minimized with respect to the plate thickness of the second collimator plate 12, the accuracy of the positioning of the second collimator plates 12 improves, but the insertion of the second collimator plates 12 through the slits 111 becomes difficult to degrade the assembly yield.

On the other hand, in the case of the present embodiment, when the second collimator plates 12 are inserted through the slits 111, the plurality of first collimator plates 11 are moved toward the top-end block 13 to align the positions of the first collimator plates 11 in the slice direction SL and cause the corresponding slits 111 to overlap each other in the channel direction CH. Accordingly, as the width of each of the slits 111 is larger, the second collimator plates 12 can be more easily inserted therethrough. Then, after the insertion of the second collimator plates 12, the plurality of first collimator plates 11 are moved toward the bottom-end block 14 such that the second collimator plates 12 are held between the individual slits 111 and the plate surfaces thereof are brought into abutment with the reference surfaces. This allows high-accuracy positioning to be performed. That is, the two-dimensional collimator module in the present embodiment has the advantage that, even when the width of the slit 111 is set relatively large with respect to the plate thickness of the second collimator plate 12, both of easy insertion of the second collimator plates 12 and high positioning accuracy can be achieved. This increases the flexibilities of the width of the slit 111 and the plate thickness of the second collimator plate 12 and allows each of them to have a suitable magnitude.

According to the present embodiment, it is possible to implement a two-dimensional collimator module having a simple structure, high positional accuracy, and high angle accuracy. In addition, the assembly of the two-dimensional collimator module is also extremely easy.

While an exemplary embodiment has been described so herein, the present invention is not limited to the exemplary embodiment described above. Accordingly, various additions and modification can be made without departing from the scope and the gist of the present invention.

For example, in the embodiment described above, the shallow grooves and the deep grooves are alternately formed in the wall surface of the bottom-end block 14, but the pattern in which the shallow grooves and the deep grooves are arranged is not limited thereto. Any pattern can be adopted as long as it allows the second collimator plates 12 to be held between the wall surfaces of the slits 111 and their positions to be determined.

Also, for example, in the embodiment described above, the main portion of each of the second collimator plates 12 has such a fan-like shape along the direction of the fan angle of the X-ray beam, but the main portion of the second collimator plate 12 may also have a rectangular shape.

Also, for example, in the embodiment described above, the shallow grooves and the deep grooves are formed in the bottom-end block 14 to allow the second collimator plates 12 to be held between the slits 111. However, it may also be possible to provide the grooves formed in the bottom-end block 14 with equal depths and provide the first collimator plates 11 with longer lengths and shorter lengths in the slice direction SL to allow the same effect to be obtained.

Note that the embodiments described herein include not only the collimator module and the assembling method thereof but also an X-ray detector in which a plurality of such collimator modules are disposed and an X-ray CT apparatus including such an X-ray detector.

The invention claimed is:

1. A two-dimensional collimator module, comprising:
   a plurality of first collimator plates arranged in a channel direction;
   a plurality of second collimator plates arranged in a slice direction and combined with the plurality of first collimator plates to form a lattice; and
   a first block and a second block that hold the plurality of first collimator plates placed therebetween in the slice direction, wherein
   each of the plurality of first collimator plates is formed with a plurality of slits each extending along a direction of radiation emitted from an X-ray focal spot and arranged in the slice direction,
   each of the plurality of second collimator plates is inserted through an associated row of the slits in the plurality of first collimator plates,
   first plate surfaces of the second collimator plates in the slice direction abut only first wall surfaces of first and second wall surfaces of the slits in the slice direction in a first set of the plurality of first collimator plates, and
   second plate surfaces of the second collimator plates opposite to the first plate surfaces abut only the second wall surfaces of the slits in a second set of the plurality of first collimator plates separate from the first set.

2. A two-dimensional collimator module according to claim 1, wherein a surface of the first block and an opposing surface of the second block are each formed with a plurality of grooves into which the first collimator plates are configured to be inserted.

3. A two-dimensional collimator module according to claim 2, wherein
   the plurality of grooves formed in the first block include grooves having equal depths in the slice direction,
   the plurality of grooves formed in the second block include a first set of grooves having a first depth in the slice direction and a second set of grooves having a second depth larger than the first depth in the slice direction,
   the first set of first collimator plates are inserted in the first set of grooves such that the first set of first collimator plates abut wall surfaces of the first set of grooves in the slice direction, and
   the second set of first collimator plates are inserted into the second set of grooves such that a space is defined between the second set of first collimator plates and wall surfaces of the second set of grooves in the slice direction.

4. A two-dimensional collimator module according to claim 3, wherein the first set of grooves and the second set of grooves are alternately arranged in the channel direction.

5. A two-dimensional collimator module according to claim 2, wherein
   the plurality of grooves formed in the first block include grooves having equal depths in the slice direction,
   the plurality of grooves formed in the second block include grooves having equal depths in the slice direction,
   the first set of first collimator plates each have a first length in a slice direction such that the first set of first collimator plates each abut at least one wall surface of the grooves in which they are inserted, and
   the second set of first collimator plates each have a second length shorter than the first length such that respective spaces are defined between the second set of first collimator plates and slice direction wall surfaces of the grooves in which they are inserted.

6. A two-dimensional collimator module according to claim 1, comprising a fixing sheet configured to be bonded to the plurality of first collimator plates on at least one of an X-ray incident surface side and an X-ray emission surface side of the two-dimensional collimator module.

7. A two-dimensional collimator module according to claim 1, wherein the plurality of first collimator plates are arranged in a fan-like configuration along the channel direction.

8. A two-dimensional collimator module according to claim 1, wherein each of the plurality of first collimator plates has a fan-like main portion along a direction of a cone angle of an X-ray emitted from the X-ray focal spot.

9. A two-dimensional collimator module according to claim 1, wherein the plurality of second collimator plates are arranged in a fan-like configuration along the direction of the cone angle of the X-ray beam emitted from the X-ray focal spot.

10. A two-dimensional collimator module according to claim 1, wherein each of the plurality of second collimator plates has a fan-like main portion along the channel direction.

11. A two-dimensional collimator module according to claim 1, wherein each of the plurality of second collimator plates has an end portion at one end in the channel direction, the end portion wider than a length of each of the slits.

12. A two-dimensional collimator module according to claim 1, wherein
a plate thickness of each of the second collimator plates is from 0.06 mm to 0.22 mm, and
a width of each of the slits is from 0.1 mm to 0.28 mm and larger than the plate thickness.

13. A two-dimensional collimator module according to claim 12, wherein the width of the slit is from 0.20 mm to 0.28 mm.

14. An X-ray detector comprising a plurality of two-dimensional collimator modules disposed on an X-ray incident surface side of the X-ray detector, wherein said two-dimensional collimator modules each comprise:
a plurality of first collimator plates arranged in a channel direction;
a plurality of second collimator plates arranged in a slice direction and combined with the plurality of first collimator plates to form a lattice; and
a first block and a second block that hold the plurality of first collimator plates placed therebetween in the slice direction, wherein
each of the plurality of first collimator plates is formed with a plurality of slits each extending along a direction of radiation emitted from an X-ray focal spot and arranged in the slice direction,
each of the plurality of second collimator plates is inserted through an associated row of the slits in the plurality of first collimator plates,
first plate surfaces of the second collimator plates in the slice direction abut first wall surfaces of first and second wall surfaces of the slits in the slice direction in a first set of the plurality of first collimator plates, and
second plate surfaces of the second collimator plates opposite to the first plate surfaces abut only the second wall surfaces of the slits in a second set of the plurality of first collimator plates separate from the first set.

15. An X-ray detector according to claim 14, wherein said two-dimensional collimator module comprises a fixing sheet configured to be bonded to the plurality of first collimator plates on at least one of an X-ray incident surface side and an X-ray emission surface side of each two-dimensional collimator module.

16. An X-ray detector according to claim 14, wherein each of the plurality of second collimator plates has an end portion at one end in the channel direction, the end portion wider than a length of each of the slits.

17. An X-ray detector according to claim 14, wherein
a plate thickness of each of the second collimator plates is from 0.06 mm to 0.22 mm, and
a width of each of the slits is from 0.1 mm to 0.28 mm and larger than the plate thickness.

18. An X-ray detector according to claim 14, wherein the width of the slit is from 0.20 mm to 0.28 mm.

19. An X-ray CT apparatus, comprising a scan gantry having an X-ray tube and an X-ray detector,
wherein said X-ray detector comprises a plurality of two-dimensional collimator modules disposed on an X-ray incident surface side of the X-ray detector, wherein said two-dimensional collimator modules each comprise:
a plurality of first collimator plates arranged in a channel direction;
a plurality of second collimator plates arranged in a slice direction and combined with the plurality of first collimator plates to form a lattice; and
a first block and a second block that hold the plurality of first collimator plates placed therebetween in the slice direction, wherein
each of the plurality of first collimator plates is formed with a plurality of slits each extending along a direction of radiation emitted from an X-ray focal spot and arranged in the slice direction,
each of the plurality of second collimator plates is inserted through an associated row of the slits in the plurality of first collimator plates,
first plate surfaces of the second collimator plates in the slice direction abut only first wall surfaces of first and second wall surfaces of the slits in the slice direction in a first set of the plurality of first collimator plates, and
second plate surfaces of the second collimator plates opposite to the first plate surfaces abut only the second wall surfaces of the slits in a second set of the plurality of first collimator plates separate from the first set.

20. A method for assembling a two-dimensional collimator module, comprising:
inserting a plurality of first collimator plates into a plurality of grooves formed in opposing surfaces of a first block and a second block;
moving the plurality of first collimator plates toward the first block to cause the plurality of first collimator plates to abut wall surfaces of the grooves in the first block such that positions of a plurality of slits formed in each of the first collimator plates align in rows;
inserting each of a plurality of second collimator plates through each row of the slits;
moving the plurality of first collimator plates toward the second block such that a first set of the plurality of first collimator plates abut wall surfaces of the grooves in the second block and a second set of the plurality of first collimator plates separate from the first set are brought closer to the wall surfaces of the grooves in the second block, such that the second collimator plates are held between a first wall surface of the slits in the first set of first collimator plates and a second wall surface of the slits in the second set of first collimator plates; and
bonding the first and second blocks and the plurality of first collimator plates to each other, while bonding the plurality of first collimator plates and the plurality of second collimator plates to each other.

* * * * *

UNITED STATES PATENT AND TRADEMARK OFFICE
CERTIFICATE OF CORRECTION

PATENT NO. : 9,020,093 B2  
APPLICATION NO. : 13/407069  
DATED : April 28, 2015  
INVENTOR(S) : Kurochi et al.

Page 1 of 1

It is certified that error appears in the above-identified patent and that said Letters Patent is hereby corrected as shown below:

IN THE CLAIMS

In Column 13, Line 55, in Claim 14, delete "abut" and insert -- abut only --, therefor.

Signed and Sealed this
Second Day of February, 2016

Michelle K. Lee
*Director of the United States Patent and Trademark Office*